United States Patent [19]

Prücher et al.

[11] Patent Number: 5,561,145
[45] Date of Patent: *Oct. 1, 1996

[54] 4-ARYLOXY- AND 4-ARYLTHIOPIPERIDINE DERIVATIVES

[75] Inventors: Helmut Prücher, Heppenheim; Rudolf Gottschlich, Reinheim; Gerd Bartoszyk, Darmstadt; Christoph Seyfried, Jugenheim, all of Germany

[73] Assignee: Merck Patent Gesellschaft Mit Beshrankter Haftung, Darmstadt, Germany

[ * ] Notice: The term of this patent shall not extend beyond the expiration date of Pat. No. 5,532,255.

[21] Appl. No.: 278,210

[22] Filed: Jul. 21, 1994

[30] Foreign Application Priority Data

Jul. 21, 1993 [DE] Germany ............ 43 24 393.2

[51] Int. Cl.⁶ ............ A61K 31/445; C07D 413/06
[52] U.S. Cl. ............ 514/326; 546/209
[58] Field of Search ............ 514/326; 546/209

[56] References Cited

U.S. PATENT DOCUMENTS

| | | | |
|---|---|---|---|
| 4,804,657 | 2/1989 | Kogure | 514/218 |
| 4,970,217 | 11/1990 | Prucher | 514/327 |
| 5,232,931 | 8/1993 | Prucher | 514/321 |

FOREIGN PATENT DOCUMENTS

| | | |
|---|---|---|
| 0300272 | 1/1989 | European Pat. Off. |
| 0443197 | 8/1991 | European Pat. Off. |

OTHER PUBLICATIONS

Duncan et al., "Aroylpiperidines and Pyrrolidines, etc.", *Journal of Medicinal Chemistry*, vol. 13, No. 1, pp. 1–6, Jan. 1970.

*Primary Examiner*—Ceila Chang
*Attorney, Agent, or Firm*—Millen, White, Zelano, & Branigan, P.C.

[57] ABSTRACT

Novel 4-aryloxy- or 4-arylthiopiperidine derivatives of the formula I

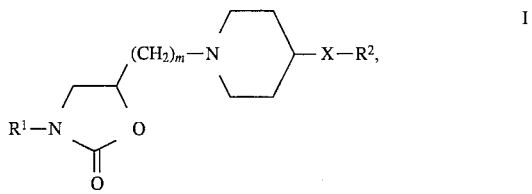

in which $R^1$ and $R^2$ are each, independently of one another, phenyl radicals which are unsubstituted or mono or disubstituted by A, OH, OA, aryloxy with 6–10 C atoms, aralkyloxy with 7–11 C atoms, $-O-(CH_2)_n-O-$, Hal, $CF_3$, $NO_2$, $NH_2$, NHA, $NA_2$, NHAc, NAAc, $NHSO_2A$ and/or $NASO_2A$, X is O, S, SO or $SO_2$, m is 1, 2 or 3, n is 1 or 2, A is an alkyl radical with 1–6 C atoms, Hal is F, Cl, Br or I and Ac is alkanoyl with 1–8 C atoms, aralkanoyl with 1–10 C atoms or aroyl with 7–11 C atoms, and the physiologically acceptable salts thereof, show an effect influencing the central nervous system, in particular neuroleptic effect, with a negligible cataleptic effect.

6 Claims, No Drawings

4-ARYLOXY- AND 4-ARYLTHIOPIPERIDINE DERIVATIVES

The invention relates to 4-aryloxy- or 4-arylthiopiperidine derivatives of the formula I

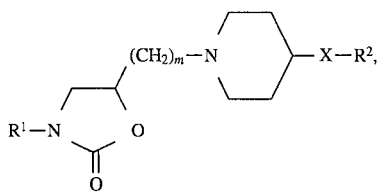

in which

R$^1$ and R$^2$ are each, independently of one another, phenyl radicals which are unsubstituted or mono- or disubstituted by A, OH, OA, aryloxy with 6–10 C atoms, aralkyloxy with 7–11 C atoms, —O—(CH$_2$)$_n$—O—, Hal, CF$_3$, NO$_2$, NH$_2$, NHA, NA$_2$, NHAc, NAAc, NHSO$_2$A and/or NASO$_2$A, X is O, S, SO or SO$_2$, m is 1, 2 or 3, n is 1 or 2, A is an alkyl radical with 1–6 C atoms, Hal is F, Cl, Br or I and Ac is alkanoyl with 1–8 C atoms, aralkanoyl with 1–10 C atoms or aroyl with 7–11 C atoms, and the physiologically acceptable salts thereof.

The invention was based on the object of finding novel compounds which can be used to produce medicaments.

It has been found that the said substances have valuable pharmacological properties while being well tolerated. Thus, for example, they show effects influencing the central nervous system, preferably depressing (for example sedative, tranquilizing, neuroleptic and/or antidepressant) effects. Specifically, the compounds have a depressing effect on the behaviour of mice (for method see Irwin, psychopharmacologica 13 (1968), 222–257). They inhibit the apomorphine-induced climbing behaviour in mice (for method see Costall et al., European J. Pharmacol. 50 (1968), 39–50) or they induce contralateral pivoting in hemiparkinson rats (determinable by the method of Ungerstedt et al., Brain Res. 24 (1970), 485–493) with negligible cataleptic side effects occurring (for method see Dolini-Stola, Pharmakopsychiat. 6 (1973), 189–197). Furthermore, the substances inhibit the binding of tritiated dopamine agonists and antagonists to striatal receptors (determinable by the method of Schwarcz et al., J. Neurochemistry 34 (1980), 772–778, and Creese et al., European J. Pharmacol. 46 (1977), 377–381). In addition, the compounds inhibit the linguomandibular reflex in the anaesthetized rat (determinable on the basis of the methods of Barnett et al., European J. Pharmacol. 21 (1973), 178–182, and of Ilhan et al., European J. Pharmacol. 33 (1975), 61–64). Furthermore, analgesic and hypotensive effects occur; thus, the arterial blood pressure measured directly is reduced in catheterized conscious, spontaneously hypertensive rats (SHR/NIH-MO//CHB-EMD strain; for method see Weeks and Jones, Proc. Soc. Exptl. Biol. Med. 104 (1960), 646–648) after intragastric administration of the compounds.

Compounds of the formula I and their physiologically acceptable acid addition salts can therefore be used as pharmaceutical active substances and as intermediates for preparing other pharmaceutical active substances.

The invention relates to the piperidine derivatives of the formula I and their salts.

The invention furthermore relates to a process for the preparation of piperidine derivatives of the formula I and the salts thereof, characterized in that a compound of the formula II

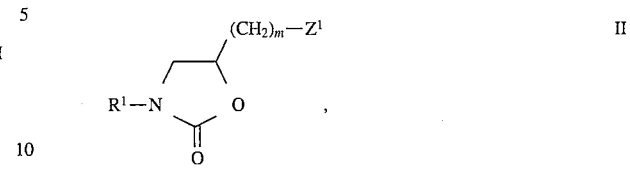

in which

R$^1$ is a phenyl radical which is unsubstituted or mono- or disubstituted by A, OH, OA, aryloxy with 6–10 C atoms, aralkyloxy with 7–11 C atoms, —O—(CH$_2$)$_n$—O—, Hal, CF$_3$, NO$_2$, NH$_2$, NHA, NA$_2$, NHAc, NAAc, NHSO$_2$A and/or NASO$_2$A, m is 1, 2 or 3, Z$^1$ is Z or NH$_2$, Z is Cl, Br, I, OH, SO$_3$CH$_3$ or another reactive functionally modified OH group, if Z$^1$=Z, is reacted with a compound of the formula III

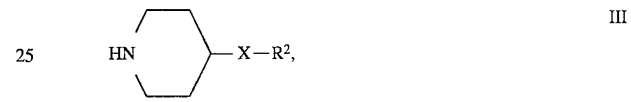

in which

R$^2$ and X have the meanings stated above, or, if Z$^1$=NH$_2$, with a compound of the formula IIIa

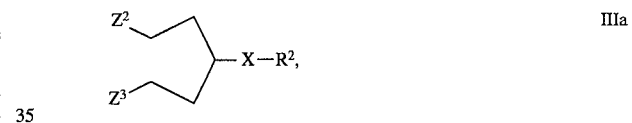

in which

R$^2$ and X have the meanings stated above, and

Z$^2$ and Z$^3$ are identical or different and each is Cl, Br, I, OH, SO$_3$CH$_3$ or another reactive functionally modified OH group, in that a compound which otherwise corresponds to the formula I but, in place of one or more hydrogen atoms, contains one or more reducible groups and/or one or more additional —SO$_2$— and/or —SO— groups is treated with a reducing agent, or in that to prepare a compound of the formula I as stated above, a radical R$^1$ and/or R$^2$ is converted into another radical R$^1$ and/or R$^2$, or in that a compound of the formula IV

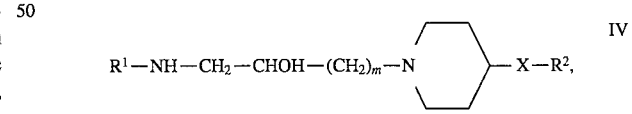

in which R$^1$, R$^2$, X and m have the above stated meanings, is reacted with a suitable reactive carbonic acid derivative, or in that a compound of the formula V

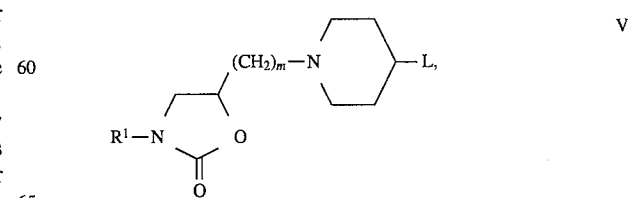

in which

R$^1$ and m have the above stated meanings and

L is Cl, Br or another suitable leaving group is reacted with a compound of the formula VI

   VI, in which

R² has the above stated meaning and

X¹ is OH, SO₂H, SH or a suitable salt-like radical derivable therefrom, and/or in that, where appropriate, a compound of the formula I is liberated from one of its functional derivatives by treatment with a solvolysing or hydrolysing agent, or a compound of the formula I is converted by reduction or oxidation into another compound of the formula I, and/or in that a base of the formula I according to claim 1 is converted by treatment with an acid into one of its salts.

Hereinbefore and hereinafter the radicals R¹, R², A, Ac, X and Hal, as well as the parameters m and n, have the meanings stated for formula I unless something different is expressly stated.

A in the formulae or part-formulae is an alkyl radical with 1–6, preferably 1, 2, 3 or 4, C atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, hexyl, 1-, 2- or 3-methylpentyl or else 2,2- or 2,3-dimethylpropyl.

The radicals R¹ and R² can be identical or different. R¹ and R² are preferably, each independently of the other, unsubstituted or substituted phenyl, it being possible for the substituents each to be in the ortho or meta, but particularly preferably in the para, position of the phenyl radical.

Specifically, R¹ and R² are preferably phenyl, p-fluoro-, p-chloro-, p-hydroxy-, p-methoxy-, p-nitro-, p-methyl-, p-tert-butyl-, p-phenylmethoxy- or p-acetamidophenyl or p-N-methylacetamidophenyl.

Furthermore, R¹ and R² can also preferably be 3,4-methylenedioxy-, p-propionylamino- or p-methylsulfonamidophenyl.

Ac is preferably acetyl or propionyl, but is also formyl, butyryl, isobutyryl, valeryl, isovaleryl, pivaloyl (trimethylacetyl), additionally preferably optionally substituted aroyl with 7–11 C atoms, one of the following groups being suitable and preferred as substituents: alkyl, alkoxy, alkylthio, alkylsulfinyl or alkylsulfonyl with, in each case, 1–3, preferably 1 or 2, C atoms, methylenedioxy, also OH, F, Cl, Br, I, NO₂, NH₂, alkylamino or dialkylamino with, in each case, 1–3, preferably 1 or 2, C atoms in the alkyl group. Individual preferred aroyl radicals are benzoyl, o-, m- or p-tolyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxybenzoyl, o-, m- or p-methylsulfonylbenzoyl, 2,3- or 3,4-methylenedioxybenzoyl or 1-2-naphthoyl. Ac can additionally be aralkanoyl with 1–10 C atoms such as, for example, phenylacetyl, 2- or 3-phenylpropionyl or 2-, 3- or 4-phenylbutyryl or 2- or 3-phenylisobutyryl.

X is preferably oxygen or sulfur, but is also preferably SO₂, while Hal is preferably F or Cl.

Accordingly, the invention particularly relates to those compounds of the formula I in which at least one of the said radicals has one of the stated meanings, in particular those stated preferred.

Some preferred groups of compounds may be represented by the following part-formulae Ia to If which correspond to the formula I and in which the undefined radicals and parameters have the meaning stated for formula I, but in which in Ia
  R¹ is p-methoxyphenyl or phenyl and R² is p-acetamidophenyl;
in Ib
  R¹ is p-methoxyphenyl and R² is phenyl, m-methoxy-, p-methoxy-, p-hydroxy-, p-chloro-, p-fluoro-, p-phenyl-methoxy-, 3,4-methylenedioxy-, p-methyl- or p-tert-butylphenyl;
in Ic
  R¹ is p-methoxyphenyl, X is oxygen and m is 1;
in Id
  R² is p-acetamidophenyl, X is oxygen and m is 1;
in Ie
  R¹ is p-methoxyphenyl, R² is p-acetamido-, p-methoxy-, p-chloro-, p-methyl-, p-tert-butyl- or p-methylsulfonamidophenyl and X is sulfur;
in If
  R¹ is p-methoxyphenyl, R² is p-acetamido-, p-methoxy- or p-methylsulfonamidophenyl and X is —SO₂—.

The compounds of the formula I are moreover prepared by methods known per se, as described in the literature (for example in the standard works such as Houben-Weyl, Methoden der Organischen Chemie (Methods of Organic Chemistry), Georg-Thieme-Verlag; J. March, Advanced Organic Chemistry 3rd. Ed. (1985) or Organic Reactions, both John Wiley & Sons, Inc. New York), specifically under reaction conditions known and suitable for the said reactions. It is moreover possible to make use of variants which are known per se but not mentioned here in detail.

The starting materials for the claimed process can, if required, also be formed in situ in such a manner that they are not isolated from the reaction mixture but immediately reacted further to give the compounds of the formula I.

Z¹ in the compounds of the formula II is preferably Z; accordingly, the compounds of the formula II are reacted in particular with piperidine derivatives of the formula III in order to obtain compounds of the formula I. The radical Z is preferably Cl or Br; however, it also be I, OH or a reactive functionally modified OH group, in particular alkylsulfonyloxy with 1–6 (for example, methanesulfonyloxy) or arylsulfonyloxy with 6–10 C atoms (for example, benzenesulfonyloxy, p-toluenesulfonyloxy, 1- or 2-naphthalenesulfonyloxy).

However, it is also possible for Z¹ in compounds of the formula II to be NH₂. Compounds of this type are then reacted with compounds of the formula IIIa in which Z² and Z³ can be identical or different and are preferably Cl or Br, but also I, OH or a reactive functionally modified OH group, preferably as indicated above.

Some of the compounds of the formulae II, III and IIIa are known; the unknown compounds of the formulae II, III and IIIa can easily be prepared in analogy to the known compounds. Primary alcohols of the formula II can be obtained, for example, by reducing the corresponding carboxylic acids or their esters. Treatment with thionyl chloride, hydrogen bromide, phosphorus tribromide or similar halogen compounds provides the corresponding halides of the formula II.

The sulfonyloxy compounds of the formula II can be obtained from the corresponding alcohols by reaction with the appropriate sulfonyl chlorides. The iodine compounds of the formula II can be obtained, for example, by the action of potassium iodide on the relevant p-toluenesulfonic esters. The amines of the formula II can be prepared, for example, from the halides with potassium phthalimide or by reducing the corresponding nitriles.

Some of the piperidines of the formula III are known, or they can be prepared in analogy to the known compounds.

They are obtained, for example, by reacting 4-halopiperidines with suitable phenolates or, for example, by reacting 4-hydroxypiperidines, it also being possible for the hydroxyl group to be functionally modified to a reactive group, with appropriate thiophenols or thiophenolates and, where appropriate, subsequent oxidation of the S group to —SO— or —$SO_2$— groups. Compounds of the formula IIIa can be prepared, for example, by reducing corresponding diesters to diols and, where appropriate, subsequent reaction with $SOCl_2$ or $PBr_3$.

The reaction of compounds II and III takes place by methods known from the literature for the alkylation of amines. It is possible to melt the components together without the presence of a solvent, where appropriate in a closed tube or in an autoclave. However, it is also possible to react the compounds in the presence of an inert solvent. Examples of suitable solvents are hydrocarbons such as benzene, toluene, xylene; ketones such as acetone, butanone; alcohols such as methanol, ethanol, isopropanol, n-butanol; ethers such as tetrahydrofuran (THF) or dioxane; amides such as dimethyl-formamide (DMF) or N-methylpyrrolidone; nitriles such as acetonitrile, where appropriate also mixtures of these solvents with one another or mixtures with water. The addition of an acid-binding agent, for example, an alkali metal or alkaline earth metal hydroxide, carbonate or bicarbonate or another salt of a weak acid of the alkali metals or alkaline earth metals, preferably potassium, sodium or calcium, or the addition of an organic base such as triethylamine, dimethylaniline, pyridine or quinoline or an excess of the amine component or of the compound of the formula III or IIIa may be beneficial. The reaction temperature depends on the conditions used and is between about 0° and 150°, normally between 20° and 130°.

It is furthermore possible to obtain a compound of the formula I by treating a precursor which, in place of hydrogen atoms, contains one or more reducible group(s) and/or one or more additional C—C and/or C—N bond(s) with a reducing agent, preferably at temperatures between −80° and +250° in the presence of at least one inert solvent.

Reducible groups (which can be replaced by hydrogen) are, in particular, oxygen in a carbonyl group, hydroxyl, arylsulfonyloxy (for example, p-toluenesulfonyloxy), N-benzenesulfonyl, N-benzyl or O-benzyl.

It is possible in principle to convert compounds which contain only one, or those which contain side by side two or more of these groups or additional bonds, into a compound of the formula I by reduction. Preferably used for this purpose is catalytic hydrogenation, nascent hydrogen or certain complex metal hydrides such as $NaBH_4$ or $LiAlH_4$.

Examples of catalysts suitable for the catalytic hydrogenation are noble metal, nickel and cobalt catalysts. The noble metal catalysts can be present on supports (for example, platinum or palladium on carbon, palladium on calcium carbonate or strontium carbonate), as oxide catalysts (for example, platinum oxide), or as fine-particle metal catalysts. Nickel and cobalt catalysts are preferably employed as Raney metals, nickel also on kieselguhr or pumice as support. The hydrogenation can be carried out at room temperature and under atmospheric pressure or else at elevated temperature and/or under elevated pressure. Preferably used are pressures between 1 and 100 at and temperatures between −80° and +150°, primarily between room temperature and 100°. The reaction is preferably carried out in the acidic, neutral or basic region and in the presence of a solvent such as water, methanol, ethanol, isopropanol, n-butanol, ethyl acetate, dioxane, acetic acid or THF; mixtures of these solvents with one another can also be used.

If nascent hydrogen is used as reducing agent, it can be generated, for example, by treating metals with weak acids or with bases. Thus, for example, a mixture of zinc with alkali metal hydroxide solution or of iron with acetic acid can be used. It is also suitable to use sodium or another alkali metal in an alcohol such as ethanol, isopropanol, butanol, amyl or isoamyl alcohol or phenol. An aluminium/nickel alloy in aqueous alkaline solution, where appropriate with the addition of ethanol, can also be used. Sodium or aluminium amalgam in aqueous alcoholic or aqueous solution is also suitable for generating nascent hydrogen. The reaction can also be carried out in heterogeneous phase, in which case an aqueous and a benzene or toluene phase is preferably used.

It is furthermore possible to employ as reducing agents complex metal hydrides such as $NaBH_4$, diisobutyl-aluminium hydride or $NaAl(OCH_2CH_2OCH_3)_2H_2$ as well as diborane, if required with the addition of catalysts such as $BF_3$, $AlCl_3$ or LiBr. Solvents particularly suitable for this purpose are ethers such as diethyl ether, di-n-butyl ether, THF, dioxane, diglyme or 1,2-dimethoxyethane as well as hydrocarbons such as benzene. Solvents suitable for a reduction with $NaBH_4$ are primarily alcohols such as methanol or ethanol, also water as well as aqueous alcohols. Reduction by these methods is preferably carried out at temperatures between −80° and +150°, in particular between 0° and about 100°.

Compounds of the formula I can furthermore be obtained by converting an aromatic radical $R^1$ and/or $R^2$ by, for example, an electrophilic substitution into another radical $R^1$ and/or $R^2$.

Compounds of the formula I can furthermore be obtained by reacting amino alcohols of the formula IV with reactive derivatives of carbonic acid. Suitable and preferred as such are dialkyl carbonates such as dimethyl or diethyl carbonate, chloroformic esters such as methyl or ethyl chloroformate, N,N'-carbonyldiimidazole or phosgene. The reaction is preferably carried out in the presence of an inert solvent, preferably a halogenated hydrocarbon such as chloroform, a hydrocarbon such as toluene, or an amide such as DMF, at temperatures between about 20° and about 200°, preferably between 100° and 150°. The carbonic acid derivative is preferably employed in excess.

In addition, compounds of the formula I can be obtained by reacting oxazolidinone derivatives of the formula V, which in turn can be obtained, for example, by reacting compounds of the formula II ($Z^1$=Z) with appropriate piperidine derivatives, with compounds of the formula VI under conditions known for the formation of ethers or thioethers.

The compounds of the formula I can also be obtained by liberating them from their functional derivatives by solvolysis, in particular hydrolysis, or by hydrogenolysis.

Preferred starting materials for the solvolysis or hydrogenolysis are those which otherwise correspond to the formula I but, in place of one or more free amino and/or hydroxyl groups, contain corresponding protected amino and/or hydroxyl groups, preferably those which, in place of an H atom linked to an N atom, have an amino protective group, in particular those which, in place of an HN group, have an R'-N group in which R' is an amino protective group, and/or those which, in place of the H atom of a hydroxyl group, have a hydroxyl protective group, for example those which correspond to the formula I but, in place of a —COOH group, have a —COOR" group in which R" is a hydroxyl protective group.

It is also possible for a plurality of identical or different protected amino and/or hydroxyl groups to be present in the molecule of the starting material. If the protective groups which are present differ from one another, they can in many cases be eliminated selectively.

The term "amino protective group" is generally known and relates to groups which are suitable for protecting (blocking) an amino group from chemical reactions but which can be easily removed after the required chemical reaction has been carried out elsewhere in the molecule. Typical groups of this type are, in particular, unsubstituted or substituted acyl, aryl (for example, 2,4-dinitrophenyl (DNP)), aralkoxymethyl (for example, benzyloxymethyl (BOM)) or aralkyl groups (for example, benzyl, 4-nitrobenzyl, triphenylmethyl). Since the amino protective groups are removed after the required reaction (or sequence of reactions), their nature and size is moreover not critical; however, those with 1–20, in particular 1–8, C atoms are preferred. The term "acyl group" is to be interpreted in the widest sense in connection with the present process. It embraces acyl groups derived from aliphatic, araliphatic, aromatic or heterocyclic carboxylic acids or sulfonic acids as well as, in particular, alkoxycarbonyl, aryloxycarbonyl and, especially, aralkoxycarbonyl groups. Examples of such acyl groups are alkanoyl such as acyl, propionyl, butyryl; aralkanoyl such as phenylacetyl; aroyl such as benzoyl or toluyl; aryloxyalkanoyl such as phenoxyacetyl; alkoxycarbonyl such as methoxycarbonyl, ethoxycarbonyl, 2,2,2-trichloroethoxycarbonyl, isopropoxycarbonyl, tert-butoxycarbonyl (BOC), 2-iodoethoxycarbonyl; aralkyloxycarbonyl such as benzyloxycarbonyl (CBZ), 4-methoxybenzyloxycarbonyl, 9-fluorenylmethoxycarbonyl (FMOC). Preferred amino protective groups are BOC, DNP and BOM, furthermore CBZ, benzyl and acetyl.

The term "hydroxyl protective group" is likewise generally known and relates to groups which are suitable for protecting a hydroxyl group from chemical reactions but which can easily be removed after the required chemical reaction has been carried out elsewhere in the molecule. Typical groups of this type are the above-mentioned unsubstituted or substituted aryl, aralkyl or acyl groups, furthermore alkyl groups. The nature and size of the hydroxyl protective groups is not critical because they are removed again after the required chemical reaction or sequence of reactions; preferred groups have 1–20, in particular 1–10, C atoms. Examples of hydroxyl protective groups are, inter alia, tertbutyl, benzyl, p-nitrobenzoyl, p-toluenesulfonyl and acetyl, with benzyl and acetyl being particularly preferred.

The compounds of the formula I are liberated from their functional derivatives, for example, depending on the protective group used, with strong acids, preferably with trifluoroacetic acid or perchloric acid, or else with other strong inorganic acids such as hydrochloric acid or sulfuric acid, strong carboxylic acids such as trichloroacetic acid or sulfonic acid such as benzene- or p-toluenesulfonic acid. The presence of an additional inert solvent is possible but not always necessary.

Suitable and preferred inert solvents are organic, for example carboxylic acids such as acetic acid, ethers such as tetrahydrofuran or dioxane, amides such as dimethylformamide (DMF), halogenated hydrocarbons such as dichloromethane, also alcohols such as methanol, ethanol or isopropanol, as well as water. Mixtures of the abovementioned solvents are also suitable.

Trifluoroacetic acid is preferably used in excess without the addition of another solvent, perchloric acid in the form of a mixture of acetic acid and 70% perchloric acid in the ratio 9:1. The reaction temperatures for the cleavage are preferably between about 0° and about 50°; between 15° and 30° (room temperature) is preferably used.

The BOC group can be eliminated, for example, preferably with 40% trifluoroacetic acid in dichloromethane or with about 3 to 5N HCl in dioxane at 15°–60°, and the FMOC group with an approximately 5–20% solution of dimethylamine, diethylamine or piperidine in DMF at 15°–50°. Elimination of the DNP group also takes place, for example, with an approximately 3–10% solution of 2-mercaptoethanol in DMF/water at 15°–30°.

Protective groups which can be removed by hydrogenolysis (for example BOM, CBZ or benzyl) can be eliminated, for example, by treatment with hydrogen in the presence of a catalyst (for example, noble metal catalyst such as palladium, preferably on a support such as carbon). Suitable solvents in this case are those mentioned above, especially, for exhale, alcohols such as methanol or ethanol or amides such as DMF. The hydrogenolysis is, as a rule, carried out at temperatures between 0°0and 100° and under pressures between 1 and 200 bar, preferably at 20°–30° and under 1–10 bar. Hydrogenolysis of the CBZ group takes place, for example, well on 5–10% Pd—C in methanol at 20°–30°.

It is furthermore possible where appropriate for a compound of the formula I to be converted by methods known per se into another compound of the formula I.

Thus, ethers (O-alkyl derivatives) can be cleaved, resulting in the corresponding hydroxyl derivatives. For example, the ethers can be cleaved by treatment with dimethyl sulfide/boron tribromide complex, for example in toluene, 1,2-dichloroethane, THF or dimethyl sulfoxide, by melting with pyridine hydrohalides or aniline hydrohalides, preferably pyridine hydrochloride, at about 150°–250°, with HBr/acetic acid or with Al trihalides in chlorinated hydrocarbons such as 1,2-dichloroethane.

The compounds of the formula I may have a centre of asymmetry. They may therefore be obtained from their preparation as racemates or, if optically active starting materials are used, also in optically active form. Resulting racemates may, if required, be separated mechanically or chemically by methods known per se into their optical antipodes. Preferably, diastereomers are formed from the racemate by reaction with an optically active resolving agent. Examples of suitable resolving agents are optically active acids such as the D and L forms of tartaric acid, dibenzoyltartaric acid, diacetyltartaric acid, camphorsulfonic acid, mandelic acid, maleic acid or lactic acid. The various forms of the diastereomers can be separated in a manner known per se, for example by fractional crystallization, and the optically active compounds of the formula I can be liberated from the diastereomers in a manner known per se.

A resulting base of the formula I can be converted with an acid into the relevant acid addition salt. Acids suitable and preferred for this reaction are those which provide physiologically acceptable salts. Thus, it is possible to use inorganic acids, for example sulfuric acid, hydrohalic acids, such as hydrochloric acid or hydrobromic acid, phosphoric acids such as orthophosphoric acid, nitric acid, sulfamic acid, as well as organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and lauryl sulfuric acid. Acid addition salts which are not physiologically acceptable (for example, picrates) may be suitable for the isolation and purification of bases of the formula I.

The free bases of the formula I can, if required, be liberated from their salts by treatment with strong bases such as sodium or potassium hydroxide or sodium or potassium carbonate.

The invention furthermore relates to the use of the compounds of the formula I and their physiologically acceptable salts for producing pharmaceutical preparations, in particular by non- chemical means. For this purpose, they can be converted together with at least one vehicle or ancillary substance and, where appropriate, in combination with one or more other active substance(s) into a suitable dosage form.

The invention furthermore relates to compositions, in particular pharmaceutical preparations, containing at least one compound of the formula I and/or one of its physiologically acceptable salts. These preparations can be used as medicaments in human or veterinary medicine. Suitable vehicles are organic or inorganic substances which are suitable for enteral (for example oral), parenteral or topical administration and do not react with the novel compounds, for example water, vegetable oils, benzyl alcohols, polyethylene glycols, gelatin, carbohydrates such as lactose or starch, magnesium stearate, talc or petrolatum. Used for enteral administration are, in particular, tablets, coated tablets, capsules, syrups, solutions, drops or suppositories, for parenteral administration are solutions, preferably oily or aqueous solutions, furthermore suspensions, emulsions or implants, and for topical application are ointments, creams or dusting powders. The novel compounds can also be lyophilized, and the resulting lyophilizates used, for example, to produce products for injection.

The stated preparations can be sterilized and/or contain ancillary substances such as lubricants, preservatives, stabilizers and/or wetting agents, emulsifiers, salts to influence the osmotic pressure, buffer substances, colorants, flavourings and/or aromatizing substances. They can, if required, also contain one or more other active substances, for example, one or more vitamins.

The compounds of the formula I and their physiologically acceptable salts can be used for the therapeutic treatment of the human or animal body and for controlling diseases, in particular schizophrenia and psychoreactive disorders and psychopathies, depressions, severe chronic pain and diseases associated with elevated blood pressure. Furthermore, the compounds can be used for the treatment of extrapyramidal disorders. The compounds are good atypical neuroleptics and show negligible cataleptic side effects when they are used.

In this connection the substances according to the invention are, as a rule, administered in analogy to known commercially available products (thioridazine, haloperidol), preferably in dosages between about 0.2 and 500 mg, in particular between 0.2 and 50 mg, per dosage unit. The daily dosage is preferably between about 0.003 and 10 mg/kg of body weight.

However, the specific dose for each particular patient depends on a wide variety of factors, for example on the efficacy of the specific compound employed, on the age, body weight, general state of health, sex, diet, time and route of administration, on the rate of excretion, drugs combination and severity of the particular disorder for which the therapy is intended. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 43 24 393.2, filed Jul. 21, 1993, are hereby incorporated by reference.

The meaning of "usual workup" in the following examples is: water is added if necessary, the mixture is extracted with dichloromethane, and the organic phase is separated off, dried over sodium sulfate, filtered, evaporated and purified by chromatography on silica gel and/or by crystallization. Temperatures are given in ° C. The $[\alpha]_D$ values were measured at 20° in dimethyl sulfoxide (DMSO).

EXAMPLES

Example 1

A solution of 3.01 g of 5-(methanesulfonyloxymethyl)-3-p-methoxyphenyl-2-oxazolidinone ("A") [obtainable by reacting 2,3-epoxy-1-propanol with N-benzyl-p-methoxyaniline to give 1-N-benzyl-p-methoxyanilino-propane-2,3-diol, hydrogenolysis to p-methoxyanilino-propane-2,3-diol, reaction with diethyl carbonate to give 5-(hydroxy-methyl)-3-p-methoxyphenyl-2-oxazolidinone and reaction with methanesulfonyl chloride], 1.58 g of 4-(p-acetamido-phenoxy)piperidine, 1.8 g of potassium iodide and 1.4 g of potassium carbonate in 100 ml of acetonitrile is boiled for 12 hours and, after cooling, worked up as usual to result in 3-p-methoxyphenyl-5-[(4-p-acetamido-phenoxypiperidino)methyl]- 2-oxazolidinone.

The following are obtained by reaction of "A"
with
4-(p-methoxyphenoxy) piperidine: 3-p-methoxyphenyl-5-[(4-p-methoxyphenoxypiperidino)methyl]-2-oxazolidinone;
with
4-(p-chlorophenoxy)piperidine: 3-p-methoxyl-5-[(4-p-chlorophenoxypiperidino)methyl]-2-oxazolidinone;
with
4-(p-fluorophenoxy)piperidine: 3-p-methoxyphenyl-5-[(4-p-fluorophenoxypiperidino)methyl]-2-oxazolidinone;
with
4-(p-phenylmethoxyphenoxy)piperidine:
3-p-methoxyphenyl-5-[(4-p-phenylmethoxyphenoxypiperidino)methyl]-2-oxazolidinone (hydrochloride);
with
4-(p-hydroxyphenoxy)piperidine:
3-p-methoxyphenyl-5-[(4-p-hydroxyphenoxy)piperidino)methyl]-2-oxazolidinone;
with
4-(3,4-methylenedioxyphenoxy)piperidine:
3-p-methoxyphenyl-5-[(4-(3,4-methylenedioxyphenoxy)piperidino)methyl]-2-oxazolidinone;
with
4-(m-methoxyphenoxy)piperidine:
3-p-methoxyphenyl-5-[(4-m-methoxyphenoxypiperidino)methyl]-2-oxazolidinone;
with
4-phenoxypiperidine:
3-p-methoxyphenyl-5-[(4-phenoxypiperidino)methyl]-2-oxazolidinone;

with
4-(p-nitrophenoxy)piperidine:
3-p-methoxyphenyl-5-[(4-p-nitrophenoxypiperidino)m-
ethyl]-2-oxazolidinone.

Example 2

In analogy to Example 1, starting from 5(R)(methane-sulfonyloxymethyl)-3-p-methoxyphenyl-2-oxazolidinone there is obtained by reaction with 4-(p-acetamidophenoxy)piperidine 3-p-methoxyphenyl-5(S)-[(4-p-acetamidophenoxypiperidino)methyl]-2-oxazolidinone (hydrochloride), m.p. 195°–196°; $[\alpha]_D=-28.8°$ (DMSO).

The following are obtained analogously by reaction of 5(R)-(methanesulfonyloxymethyl)-3-p-methoxyphenyl-2-oxazolidinone
with
4-(p-methoxyphenoxy)piperidine:
3-p-methoxyphenyl-5(S)-[(4-p-methoxyphenoxypiperidino)methyl]-2-oxazolidinone (hydrochloride), m.p. 249°–250°; $[\alpha]_D=-27.8°$ (DMSO);
with
4-(p-chlorophenoxy)piperidine:
3-p-methoxyphenyl-5(S)-[(4-p-chlorophenoxypiperidino)methyl]-2-oxazolidinone (hydrochloride), m.p. 249°–251°; $[\alpha]_D=-29.9°$ (DMSO);
with
4-(p-fluorophenoxy)piperidine:
3-p-methoxyphenyl-5(S)-[(4-p-fluorophenoxypiperidino)methyl]-2-oxazolidinone (hydrochloride), m.p. 246°–247°; $[\alpha]_D=-28.9°$ (DMSO);
with
4-(p-phenylmethoxyphenoxy)piperidine:
3-p-methoxyphenyl-5(S)-[(4-p-phenylmethoxyphenoxypiperidino)methyl]-2-oxazolidinone (hydrochloride), m.p. 260°–261°; $[\alpha]_D=-26.0°$ (DMSO);
with
4-(p-hydroxyphenoxy)piperidine:
3-p-methoxyphenyl-5(S)-[(4-p-hydroxyphenoxypiperidino)methyl]-2-oxazolidinone (hydrochloride), m.p. 190°–191°; $[\alpha]_D=-30.3°$ (DMSO);
with
4-(3,4-methylenedioxyphenoxy)piperidine:
3-p-methoxyphenyl-5(S)-[(4-(3,4-methylenedioxyphenoxy)piperidino)methyl]-2- oxazolidinone (hydrochloride), m.p. 227°–229°; $[\alpha]_D=-28.9°$ (DMSO);
with
4-m-methoxyphenoxy)piperidine:
3-p-methoxyphenyl-5(S)-[(4-m-methoxyphenoxypiperidino)methyl]-2-oxazolidinone (hydrochloride), m.p. 208°–209°; $[\alpha]_D=-29.1°$ (DMSO);
with
4-(p-methanesulfonylamidophenoxy)piperidine:
3-p-methoxyphenyl-5(S)-[(4-p-methanesulfonylamido-phenoxypiperidino)methyl]-2-oxazolidinone (hydrochloride), m.p. 184° (d); $[\alpha]_D=-26.5°$ (DMSO);
with
4-phenoxypiperidine:
3-p-methoxyphenyl-5(S)-[(4-phenoxypiperidino)methyl]-2-oxazolidinone (hydrochloride), m.p. 227°–229°; $[\alpha]_D=-31.6°$ (DMSO);
with
4-(p-nitrophenoxy)piperidine:
3-p-methoxyphenyl-5(S)-[(4-p-nitrophenoxypiperidino)methyl]-2-oxazolidinone (hydrochloride), m.p. 250°–253°; $[\alpha]_D=-32.7°$ (DMSO).

Example 3

In analogy to Example 1, starting from 5(R)-(methane-sulfonyloxymethyl)-3-p-methoxyphenyl-2-oxazolinone there is obtained by reaction with 4-(p-acetamidophenylthio)piperidine 3-p-methoxyphenyl-5(S)-[(4-p-acetamidophenylthiopiperidino)methyl]-2-oxazolidinone, m.p. 178°–179°; $[\alpha]_D=-27.6°$ (DMSO).

The following are obtained analogously by reaction of 5(R)-(methanesulfonyloxymethyl)-3-p-methoxyphenyl-2-oxazolidinone
with
4-(p-methoxyphenylthio)piperidine:
3-p-methoxyphenyl-5(S)-[(4-p-methoxyphenylthiopiperidino)methyl]-2-oxazolidinone (hydrochloride), m.p. 223°–225°; $[\alpha]_D=-31.3°$ (DMSO);
with
4-(p-chlorophenylthio)piperidine:
3-p-methoxyphenyl-5(S)-[(4-p-chlorophenylthiopiperidino)methyl]-2-oxazolidinone (hydrochloride), m.p. 233°–236°; $[\alpha]_D=-30.8°$ (DMSO);
with
4-(p-methylphenylthio)piperidine:
3-p-methoxyphenyl-5(S)-[(4-p-methylphenylthiopiperidino)methyl]-2-oxazolidinone (hydrochloride), m.p. 226°–229°; $[\alpha]_D=-33.6°$ (DMSO);
with
4-(p-tert-butylphenylthio)piperidine:
3-p-methoxyphenyl-5(S)-[(4-p-tertbutylphenylthiopiperidino)methyl]-2-oxazolidinone (hydrochloride), m.p. 231°–234°; $[\alpha]_D=-30.9°$ (DMSO);
with
4-(p-methanesulfonylamidophenylthio)piperidine:
3-p-methoxyphenyl-5(S)-[(4-p-methanesulfonylamidophenylthiopiperidino)methyl]-2-oxazolidinone, m.p. 152°–154°; $[\alpha]_D=-27.1°$ (DMSO);

Example 4

A solution of 1.2 g of 3-p-methoxyphenyl-5(S)-[4-p-nitrophenoxypiperidino)methyl]-2-oxazolidinone (m.p. 250°–253°; obtainable as in Example 2) in 40 ml of methanol is hydrogenated on 0.6 g of Raney Ni at room temperature until $H_2$ uptake ceases [$p(H_2)=1$ bar]. After filtration and the usual workup, 3-p-methoxyphenyl-5(S)-4-p-aminophenoxypiperidino)methyl]-2-oxazolidinone is obtained, m.p. 236°–240°; $[\alpha]_D=-27.2°$ (DMSO).

Example 5

1 ml of propionyl chloride is added dropwise to a solution of 1.4 g of 3-p-methoxyphenyl-5(S)-[(4-p-aminophenoxypiperidino)methyl]-2-oxazolidinone and 2 ml of pyridine in 60 ml of THF, and the mixture is stirred at room temperature for 2 h. The usual workup results in 3-p-methoxyphenyl-5(S)-[(4-p-propionylaminophenoxy-piperidino)methyl]-2-oxazolidinone, m.p. 170°–172°; $[\alpha]_D=-29.4°$ (DMSO).

The following is obtained analogously by acylation of 3-p-methoxyphenyl-5(S)-[(4-p-aminophenoxypiperidino)methyl]-2-oxazolidinone with acetyl chloride:
3-p-methoxyphenyl-5(S)-[(4-p-acetamidophenoxypiperidino)methyl]-2-oxazolidinone (hydrochloride), m.p. 195°–196°; $[\alpha]_D=-28.8°$ (DMSO).

Example 6

0.5 g of NaH and 1.7 ml of ethyl iodide are added to a solution of 2.8 g of 3-p-methoxyphenyl-5(S)-[(4-p-acetamidophenoxypiperidino)methyl]-2-oxazolidinone (m.p.)

195°–196°) in 40 ml of dimethylformamide while cooling in ice, and the mixture is stirred for 1 hour. It is subsequently stirred at room temperature for a further 2 hours, and the usual workup results in 3-p-methoxyphenyl-5 -[(4-(p-N-ethylacetamidophenoxy)piperidino)-methyl]-2-oxazolidinone.

The following is obtained analogously by alkylation of the secondary N atom of the corresponding compound of the formula I:
from
3-p-methoxyphenyl-5(S)-[(4-p-acetamidophenoxypiperidino)methyl]-2-oxazolidinone with methyl iodide:
3-p-methoxyphenyl-5(S)-[(4-(p-N-methylacetamidophenoxy)piperidino)methyl]-2-oxazolidinone (hydrochloride), m.p. 254°–257°; $[\alpha]_D=-28.4°$ (DMSO).

Example 7

In analogy to Example 1, starting from 5 (R)-(methanesulfonyloxymethyl )-3-phenyl-2-oxazolidinone there is obtained by reaction with 4-(p-acetamidophenoxy)piperidine 3-phenyl-5(S)-[(4-p-acetamidophenoxypiperidino)methyl]-2-oxazolidinone (hydrochloride), m.p. >260°; $[\alpha]_D=-27.1°$ (DMSO).

The following are obtained analogously by reaction of 4-(p-acetamidophenoxy)piperidine
with
5(S)-(methanesulfonyloxymethyl)-3-phenyl-2-oxazolidinone:
3-phenyl-5(R)-[(4-p-acetamidophenoxypiperidino)-3-phenyl-2-methyl]-2-oxazolidinone (hydrochloride) m.p. >260°;
with
5(S)-(methanesulfonyloxymethyl)-3-p-chloro-phenyl-2oxazolidinone:
3-p-chlorophenyl-5(R)-[(4-p-acetamidophenoxypiperidino)methyl]-2-oxazolidinone (hydrochloride) m.p. 264°–266°;
with
5(R)-(methanesulfonyloxymethyl)-3-p-chlorophenyl-2-oxazolidinone:
3-p-chlorophenyl-5(S)-[(4-p-acetamidophenoxypiperidino)methyl]-2-oxazolidinone (hydrochloride) m.p. 264°–266°; $[\alpha]_D=-31.7°$ (DMSO);
with
5(S)-(methanesulfonyloxymethyl)-3-p-(phenylmethoxy)-phenyl-2-oxazolidinone:
  3-p-(phenylmethoxy)phenyl-5(R)-[(4-p-acetamidophenoxypiperidino)methyl]-2-oxazolidinone (hydrochloride hydrate), m.p. 189°–191°;
with
5(R)-(methanesulfonyloxymethyl)-3-p-(phenylmethoxy)phenyl-2-oxazolidinone:
3-p-(phenylmethoxy)phenyl-5(S)-[(4-p-acetamidophenoxypiperidino)methyl]-2-oxazolidinone (hydrochloride hydrate), m.p. 189°–191°; $[\alpha]_D=-22.7°$ (DMSO);
with
5(S)-(methanesulfonyloxymethyl)-3-p-hydroxyphenyl-2oxazolidinone:
3-p-hydroxyphenyl-5(R)-[(4-p-acetamidophenoxypiperidino)methyl]-2-oxazolidinone (hydrochloride), m.p. 282°–284°;
with
5(R)-(methanesulfonyloxymethyl)-3-p-hydroxyphenyl-2oxazolidinone:
3-p-hydroxyphenyl-5(S)-[(4-p-acetamidophenoxypiperidino)methyl]-2-oxazolidinone (hydrochloride), m.p. 282°–284°; $[\alpha]_D=-25.5°$ (DMSO);
with
5(S)-(methanesulfonyloxymethyl)-3-p-fluorophenyl-2oxazolidinone:
3-p-fluorophenyl-5(R)-[(4-p-acetamidophenoxypiperidino)methyl]-2-oxazolidinone (hydrochloride), m.p. 267°–268°;
with
5(R)-(methanesulfonyloxymethyl)-3-p-fluorophenyl-2-oxazolidinone:
3-p-fluorophenyl-5(S)-[(4-p-acetamidophenoxypiperidino)methyl]-2-oxazolidinone (hydrochloride), m.p. 267°–268°; $[\alpha]_D=-25.5°$ (DMSO);
with
5(S)-methanesulfonyloxymethyl)-3-p-methoxyphenyl-2-oxazolidinone:
3-p-methoxyphenyl-5(R)-[(4-p-acetamidophenoxypiperidino)methyl]-2-oxazolidinone (hydrochloride), m.p. 206°–208°; $[\alpha]^D=+29.9°$ (DMSO).

Example 8

In analogy to Example 1, starring from 5-(2-methanesulfonyloxyethyl)-3-p-methoxyphenyl-2-oxazolidinone there is obtained by reaction with 4-(p-acetamidophenoxy)piperidine 3-p-methoxyphenyl-5-[2-(4-p-acetamidophenoxypiperidino)ethyl]-2-oxazolidinone, m.p. 226°–229°.

The following are obtained analogously by reacting 5-(2-methanesulfonyloxyethyl)-3-p-methoxyphenyl-2-oxazolidinone
with
4-(p-methoxyphenoxy) piperidine:
3-p-methoxyphenyl-5-[2-(4-p-methoxyphenoxypiperidino)-ethyl]-2-oxazolidinone;
with
4-(p-chlorophenoxy)piperidine:
3-p-methoxyphenyl-5-[2-(4-p-chlorophenoxypiperidino)ethyl]-2-oxazolidinone;
with
4-(p-fluorophenoxy)piperidine:
3-p-methoxyphenyl-5-[2-(4-p-fluorophenoxypiperidino)ethyl]-2-oxazolidinone;
with
4-(p-phenylmethoxyphenoxy)piperidine:
3-p-methoxyphenyl-5-[2-(4-p-phenylmethoxyphenoxypiperidino)ethyl]-2-oxazolidinone;
with
4-(p-hydroxyphenoxy)piperidine:
3-p-methoxyphenyl-5-[2-(4-p-hydroxyphenoxypiperidino)-ethyl]-2-oxazolidinone;
with
4-(3,4-methylenedioxyphenoxy)piperidine:
3-p-methoxyphenyl-5-[2-(4-(3,4-methylenedioxyphenoxy)piperidino)ethyl]-2-oxazolidinone;
with
4-(m-methoxyphenoxy)piperidine:
3-p-methoxyphenyl-5-[2-(4-m-methoxyphenoxypiperidino)-ethyl]-2-oxazolidinone;
with
4-phenoxypiperidine:
3-p-methoxyphenyl-5-[2-(4-phenoxypiperidino)ethyl]-2-oxazolidinone;
with
4-(p-nitrophenoxy)piperidine:
3-p-methoxyphenyl -5-[2-(4-p-nitrophenoxypiperidino)ethyl]-2-oxazolidinone;

The following are obtained analogous by reacting 5-(3-methanesulfonyloxypropyl)-3-p-methoxyphenyl-2-oxazolidinone with
4-(p-acetamidophenoxy)piperidine:
3-p-methoxyphenyl -5-[3-(4-p-acetamidophenoxypiperidino)propyl]-2-oxazolidinone (dihydrochloride), m.p. 166°–168°;
with
4-(p-methoxyphenoxy)piperidine:
3-p-methoxyphenyl-5-[3-(4-p-methoxyphenoxypiperidino)-propyl]-2-oxazolidinone (hydrochloride);
with
4-(p-chlorophenoxy)piperidine:
3-p-methoxyphenyl-5-[3-(4-p-chlorophenoxypiperidino)-propyl]-2-oxazolidinone;
with
4-(p-fluorophenoxy)piperidine:
3-p-methoxyphenyl-5-[3-(4-p-fluorophenoxypiperidino)-propyl]-2-oxazolidinone;
with
4-(p-phenylmethoxyphenoxy)piperidine:
3-p-methoxyphenyl-5-[3-(4-p-phenylmethoxyphenoxypiperidino)propyl]-2-oxazolidinone;
with
4-(p-hydroxyphenoxy)piperidine:
3-p-methoxyphenyl-5-[3-(4-p-hydroxyphenoxypiperidino)propyl]-2-oxazolidinone;
with
4-(3,4-methylenedioxyphenoxy)piperidine:
3-p-methoxyphenyl-5-[3-(4-(3,4-methylenedioxyphenoxy)piperidino)propyl]-2-oxazolidinone;
with
4-(m-methoxyphenoxy)piperidine:
3-p-methoxyphenyl-5-[3-(4-m-methoxyphenoxypiperidino)-propyl]-2-oxazolidinone;
with
4 -phenoxypiperidine:
3-p-methoxyphenyl-5-[3-(4-phenoxypiperidino)propyl]2-oxazolidinone;
with
4-(p-nitrophenoxy)piperidine:
3-p-methoxyphenyl-5-[3-(4-p-nitrophenoxypiperidino)propyl]-2-oxazolidinone;

Example 9

The following are obtained by alkylation of the secondary N atom of the following compounds of the formula I in analogy to Example 6:
from
3-phenyl-5(R)-[(4-p-acetamidophenoxypiperidino)methyl]-2-oxazolidinone:
3-phenyl-5(R)-[(4-p-(N-methylacetamidophenoxy)piperidino)methyl]-2-oxazolidinone;
from
3-p-chlorophenyl-5(R)-[(4-p-acetamidophenoxypiperidino)methyl]-2-oxazolidinone:
3-p-chlorophenyl-5(R)-[(4-p-(N-methylacetamidophenoxy)piperidino)methyl]-2-oxazolidinone;
from
3-p-chlorophenyl-5(S)-[(4-p-acetamidophenoxypiperidino)methyl-2-oxazolidinone:
3-p-chlorophenyl-5(S)-[(4-p-(N-methylacetamidophenoxy)piperidino)methyl-2-oxazolidinone;
from
3-p-(phenylmethoxy) phenyl-5(R)-[(4-p-acetamidophenoxypiperidino)methyl]-2-oxazolidinone:
3-p-(phenylmethoxy)phenyl-5(R)-[(4-p-(N-methylacetamidophenoxy)piperidino)methyl]-2-oxazolidinone;
from
3-p-(phenylmethoxy)phenyl-5(S)-[(4-p-acetamidophenoxypiperidino)methyl]-2-oxazolidinone:
3-p-(phenylmethoxy)phenyl-5(S)-[(4-p-(N-methylacetamidophenoxy)piperidino)methyl]-2-oxazolidinone;
from
3-p-hydroxyphenyl-5 (R)-[(4-p-acetamido-phenoxypiperidino)methyl]-2-oxazolidinone:
3-p-methoxyphenyl-5(R)-[(4-p-(N-methylacetamidophenoxy)piperidino)methyl]-2-oxazolidinone;
from
3-p-hydroxyphenyl-5(S)-[(4-p-acetamidophenoxypiperidino)methyl]-2-oxazolidinone:
3-p-methoxyphenyl-5(S)-[(4-p-(N-methylacetamidophenoxy)piperidino)methyl]-2-oxazolidinone;
from
3-p-fluorophenyl-5(R)-[(4-p-acetamidophenoxypiperidino)methyl]-2-oxazolidinone:
3-p-fluorophenyl-5(R)-[(4-p-(N-methylacetamidophenoxy)piperidino)methyl]-2-oxazolidinone;
from
3-p-fluorophenyl-5(S)-[(4-p-acetamidophenoxypiperidino)methyl]-2-oxazolidinone:
3-p-fluorophenyl-5(S)-[(4-p-(N-methylacetamidophenoxy)piperidino)methyl]-2-oxazolidinone;
from
3-p-methoxyphenyl-5(R)-[(4-p-acetamidophenoxypiperidino)methyl]- 2-oxazolidinone:
3-p-methoxyphenyl-5(R)-[(4-p-(N-methylacetamidophenoxy)piperidino)methyl]-2-oxazolidinone:

Example 10

A solution of 1.2 g of 3-p-methoxyphenyl-5(S)-[(4-p-acetamidophenylthiopiperidino)methyl]-2-oxazolidinone (m.p. 178°–179°) and 10 equivalents of hydrogen peroxide solution (30%) in 100 ml of methanol is heated at 60° for 3 hours. Evaporation and the usual workup result in 3-p-methoxyphenyl-5(S)-[(4-p-acetamidophenylsulfonylpiperidino)methyl]- 2-oxazolidinone, m.p. 174°–176°; $[\alpha]_D = -24.0°$ (DMSO).

The following are obtained analogously by oxidation of the corresponding thiopiperidine derivatives:
from
3-p-methoxyphenyl-5(S)-[(4-p-methoxyphenylthiopiperidino)methyl]-2-oxazolidinone (hydrochloride; m.p. 225°–225°):
3-p-methoxyphenyl-5(S)-[(4-p-methoxyphenylsulfonylpiperidino)methyl]-2-oxazolidinone (hydrochloride), m.p. 254°–256°; $[\alpha]_D = -31.6°$ (DMSO);
from
3-p-methoxyphenyl-5(S)-[(4-p-chlorophenylthiopiperidino)methyl]-2-oxazolidinone (hydrochloride; m.p. 236°–236°):
3-p-methoxyphenyl-5(S)-[(4-p-chlorophenylsulfonylpiperidino)methyl]-2-oxazolidinone;
from
3-p-methoxyphenyl-5(S)-[(4-(p-methylphenylthio)piperidino)methyl]-2-oxazolidinone (hydrochloride; m.p. 229°–236°):
3-p-methoxyphenyl-5(S)-[(4-p-methylphenylsulfonylpiperidino)methyl]-2-oxazolidinone;
from
3-p-methoxyphenyl-5(S)-[(4-(p-tert-butylphenylthio)piperidino)methyl]-2-oxazolidinone (hydrochloride; m.p. 234°–234°):

3-p-methoxyphenyl-5(S)-[(4-(p-tert-butylphenylsulfonyl)piperidino)methyl]-2-oxazolidinone;
from
3-p-methoxyphenyl-5(S)-[(4-p-methanesulfonylamidophenylthiopiperidino)methyl]-2oxazolidinone (m.p. 152°–154°):
3-p-methoxyphenyl-5(S)-[(4-p-methanesulfonylamidophenylsulfonylpiperidino)methyl]-2-oxazolidinone, m.p. 187°–189°; $[\alpha]_D=-23.2°$ (DMSO).

Example 11

A solution of 1.6 g of 3-p-methoxyphenyl -5(S)-[4-p-aminophenoxypiperidino)methyl]-2-oxazolidinone [obtainable as in Example 4] and 0.9 g of methanesulfonyl chloride (dissolved in 5 ml of THF) in 100 ml of THF is stirred at room temperature for 3 hours. Evaporation and the usual workup result in 3-p-methoxyphenyl-5(S)-[(4-p-methanesulfonylaminophenoxypiperidino)methyl]-2-oxazolidinone (hydrochloride), m.p. 184° (d); $[\alpha]_D=-26.5°$ (DMSO).

Starting from 3-p-methoxyphenyl-5-[2-(4-p-aminophenoxypiperidino)ethyl]-2-oxazolidinone there is obtained analogously 3-p-methoxyphenyl-5-[2-(4-p-methanesulfonylaminophenoxypiperidino)ethyl]-2-oxazolidinone Example 12

In analogy to Example 1, starting from 5(R)-(methanesulfonyloxymethyl)-3-p-methoxyphenyl-2-oxazolidinone there is obtained by reaction with 4-(3,4-ethyleneoxy-phenoxy)piperidine:
3-p-methoxyphenyl-5(S)-[(4-(3,4-ethylendioxy-phenoxypiperidino)methyl]-2-oxazolidinone (hydrochloride) m.p. 219°–221°; $[\alpha]_D=-28.5°$ (DMSO).

The following are obtained analogously by reaction of 5(R)-(methanesulfonyloxymethyl)-3-p-methoxyphenyl-2-oxazolidinone
with
4-(o-acetamido-phenoxy)piperidine:
3-p-methoxyphenyl-5(S)-[(4-o-acetamido-phenoxypiperidino)methyl]-2-oxazolidinone, m.p. 98°–102°; $[\alpha]_D=-22.5°$ (DMSO);
with
4-(m-acetamido-phenoxy)piperidine:
3-p-methoxyphenyl-5(S)-[(4-m-acetamido-phenoxypiperidino)methyl-2-oxazolidinone, m.p. 164°–165°;$[\alpha]_D=-30.5°$ (DMSO);
with
4-(p-formamido-phenoxy)piperidine:
3-p-methoxyphenyl-5(S)-[(4-p-formamido-phenoxypiperidino)methyl]-2-oxazolidinone, m.p. 102°–103°; $[\alpha]_D=-31.2°$ (DMSO);
with
4-(p-valerylamino-phenoxy)piperidine:
3-p-methoxyphenyl-5(S)-[(4-p-valerylamino-phenoxypiperidino)methyl]-2-oxazolidinone (hydrochloride), m.p. 224°–226°; $[\alpha]^D=-26.7°$ (DMSO);
with
4-(p-isobutyrylamino-phenoxy)piperidine:
3-p-methoxyphenyl-5(S)-[(4-p-isobutyrylamino-phenoxypiperidino)methyl]-2-oxazolidinone (hydrochloride), m.p. 235°–236°; $[\alpha]_D=-28.6°$ (DMSO).

Example 13

In analogy to Example 1, starting from 5(R)-(methanesulfonyloxy-methyl)-3-p-hydroxyphenyl-2-oxazolidinone there is obtained by reaction with 4-(p-hydroxy-phenoxy)piperidine:
3-p-hydroxyphenyl-5(S)-[(4-p-hydroxy-phenoxypiperidino)methyl]-2-oxazolidinone (hydrochloride), m.p. 241°–245°; $[\alpha]_D=-28°$ (DMSO).

The following is obtained analogously by reaction of 5(R)-(methanesulfonyloxymethyl)-3-p-hydroxyphenyl-2-oxazolidinone
with
4-(p-propionylamino-phenoxy)piperidine:
3-p-hydroxyphenyl-5(S)-[(4-p-propionylaminophenoxypiperidino)methyl]-2-oxazolidinone, m.p. 122°–125°; $[\alpha]_D=-25.0°$ (DMSO).

The following examples relate to pharmaceutical preparations.

Example A

Injection vials

A solution of 100 g of an active substance of the formula I and 5 g of disodium hydrogen phosphate in 3 l of double-distilled water is adjusted to pH 6.5 with 2N hydrochloric acid, sterilized by filtration, dispensed into injection vials, lyophilized and closed sterile. Each injection vial contains 5 mg of active substance.

Example B

Suppositories

A mixture of 20 mg of an active substance of the formula I is melted with 100 g of soya lecithin and 1400 g of cocoa butter, poured into moulds and left to cool. Each suppository contains 20 mg of active cool. Each suppository contains 20 mg of active substance.

Example C

Solution

A solution of 1 g of an active substance of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. The solution is adjusted to pH 6.8, made up to 1 l and sterilized by irradiation. This solution can be used in the form of eyedrops.

Example D

Ointment 500 mg of an active substance of the formula I are mixed with 99.5 g of petrolatum under aseptic conditions.

Example E

Tablets

A mixture of 1 kg of active substance of the formula I, 4 kg of lactose, 1.2 kg of potato starch, 0.2 kg of talc and 0.1 kg of magnesium stearate is compressed to tablets in a conventional manner so that each tablet contains 10 mg of active substance.

Example F

Coated tablets

Tablets are compressed in analogy to Example E and are subsequently coated in a conventional way with a coating of sucrose, potato starch, talc, tragacanth and colorant.

Example G

Capsules 2 kg of active substance of the formula I are packed in hard gelatin capsules in a conventional way so that each capsule contains 20 mg of the active substance.

Example H

Ampoules

A solution of 1 kg of active substance of the formula I in 60 l of double-distilled water is dispensed into ampoules, lyophilized under aseptic conditions and sealed sterile. Each ampoule contains 10 mg of active substance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 4-Arloxy-or 4-arylthiopiperidine derivatives of the formula

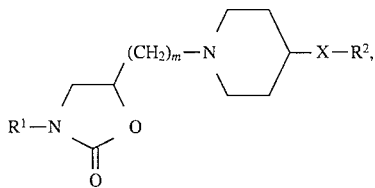

in which

R$^1$ and R$^2$ are each, independently of one another, phenyl radicals which are unsubstituted or mono- or disubstituted by A, OH, OA, aryloxy with 6–10 C atoms, aralkyloxy with 7–11 C atoms, —O—(CH$_2$)$_n$—O—, Hal, CF$_3$, NO$_2$, NH$_2$, NHA, NA$_2$, NHAc, NAAc, NHSO$_2$A and/or NASO$_2$A, X is O, S, SO or SO$_2$, m is 1, 2 or 3, n is 1 or 2, A is an alkyl radical with 1–6 C atoms, Hal is F, Cl, Br or I and Ac is formyl, C$_{1-7}$ carbonyl, phenyl-C$_{1-4}$ carbonyl, phenylcarbonyl, or naphthyl-carbonyl and the physiologically acceptable salts thereof.

2. A compound of the formula I according to claim 1 which is an enantiomer.

3. (a) 3-p-chlorophenyl-5-[(4-p-acetamidophenoxypiperidino)methyl]-2oxazolidinone;

(b) 3-p-hydroxyphenyl-5-[(4-p-acetamidophenoxypiperidino)methyl]-2-oxazolidinone;

(c) 3-p-methoxyphenyl-5-[(4-p-chlorophenoxypiperidino)methyl]-2-oxazolidinone;

(d) 3-p-methoxyphenyl-5-[(4-p-hydroxyphenoxypiperidino)methyl]-2-oxazolidinone;

(e) 3-p-methoxyphenyl-5-[(4-p-nitrophenoxypiperidino)methyl]-2-oxazolidinone;

(f) 3-p-methoxyphenyl-5-[(4-p-chlorophenylthiopiperidino)methyl]-2-oxazolidinone;

(g) 3-p-methoxyphenyl-5-[(4 -p-methylphenylthiopiperidino)methyl]-2-oxazolidinone;

(h) 3-p-methoxyphenyl-5-[(4-p-methoxyphenylsulfonylpiperidino)methyl]-2-oxazolidinone.

4. A racemic mixture of compounds of the formula I according to claim 1.

5. A diastereomer of a compound of the formula I according to claim 1.

6. A pharmaceutical composition characterized by containing a compound selected from the group consisting of compounds of formula I according to claim 1, and physiologically acceptable salts thereof, together with a pharmaceutically acceptable vehicle.

* * * * *